US00PP19758P2

(12) United States Plant Patent
Easey

(10) Patent No.: US PP19,758 P2
(45) Date of Patent: Feb. 24, 2009

(54) LIVE OAK TREE NAMED 'FBQV22'

(50) Latin Name: *Quercus virginiana*
Varietal Denomination: FBQV22

(75) Inventor: Norman C. Easey, Sarasota, FL (US)

(73) Assignee: Fish Branch Tree Farm, Inc., Zolfo Springs, FL (US)

( * ) Notice: Subject to any disclaimer, the term of this patent is extended or adjusted under 35 U.S.C. 154(b) by 74 days.

(21) Appl. No.: 11/647,916

(22) Filed: Dec. 28, 2006

(51) Int. Cl.
*A01H 5/00* (2006.01)

(52) U.S. Cl. ..... Plt./225
(58) Field of Classification Search ..... Plt./225
See application file for complete search history.

(56) References Cited

U.S. PATENT DOCUMENTS

PP11,097 P * 10/1999 Sallin
PP11,219 P * 2/2000 Strickland
PP12,015 P2 * 7/2001 Reeves

* cited by examiner

*Primary Examiner*—Kent L Bell
(74) *Attorney, Agent, or Firm*—Klarquist Sparkman, LLP

(57) ABSTRACT

A distinct variety of live oak (*Quercus virginiana*) named 'FBQV22' which is distinctive in having a dense, pyramidal shaped, upright canopy; a dominant central leader; well placed scaffold branches and numerous small lateral spur branches, generally without included bark in the branch unions; mature dark foliage with leaves typically being about one and one-quarter inch to about two and one-half inches long and about three-eighths to about one-half inch wide; and an evergreen habit. The canopy is very dense with interior and exterior foliage provided by interior spur branches.

3 Drawing Sheets

Latin name of genus and species: *Quercus virginiana.*
Variety denomination: 'FBQV22'.

BACKGROUND OF THE INVENTION

The present invention relates to a new and distinct variety of *Quercus virginiana* (Live oak) referred to by the varietal name 'FBQV22'.

The original 'FBQV22' tree was initially discovered as a seedling growing in a cultivated area of the Fish Branch Tree Farm, in Zolfo Springs, Fla., among a group of cultivated Live Oak seedlings. These seedlings had been acquired from a grower of "liners" when they were about twelve to fourteen inches tall. These seedlings had been grown from seed. The parent trees of these seedlings and therefore of the original tree of this new variety are both unknown to the inventor.

'FBQV22' was observed to have an upright habit of growth and a dominant leader, relatively dark-green foliage color compared to common seedling Live Oak trees observed by the inventor, dense foliage arrangement, and true evergreen habit. Compared to common seedling Live Oak trees observed by the inventor, this initially discovered tree had a rapid growth rate, generally lacked included bark in branches, had numerous small diameter lateral spur branches, had leaves which typically are about one and one-quarter inch to two and one-half inches long by about three-eights inch to about one-half inch wide and which were consistently relatively dark green when mature, and exhibited a dense, upright, pyramidal canopy. These characteristics of my new variety have been observed to be fixed and reproduce true to type in progeny asexually propagated from cuttings from the initially discovered tree. Asexual propagation was performed at a nursery in Zolfo Springs, Fla.

BRIEF SUMMARY OF THE INVENTION

The 'FBQV22' variety has not been observed under all growing conditions and thus variations may occur as a result of different growing conditions. The observations are of the original tree and five year old asexually propagated trees of my new variety growing in Zolfo Springs, Fla. and in Sarasota, Fla.

'FBQV22' has an unusually narrow, pyramidal canopy as a juvenile of 4 years (from a cutting) or less with consistently dark green and truly evergreen foliage compared to the species in general. Later, (beginning in the 5th or 6th year), it has a broader width to height ratio as compared to its nearest variety 'SDLN' (U.S. Plant Pat. No. 12,015). At nine years of age, the original tree of my variety had a width to height ratio of about 0.68 (height to width ratio 1.47). A group of ten typical five year old asexually propagated trees of my new variety growing in Zolfo Springs, Fla., had an average width to height ratio of about 0.57 (10 feet wide to 17.7 feet tall). The height to width ratio was about 1.77.

The leaves of 'FBQV22' variety are a slightly darker green than those of common seedling Live Oak trees which I have observed growing in the same general area and mature leaves have been observed to not change color significantly with the seasons.

Unlike the common seedling Live Oak trees I have observed, the 'FBQV22' variety has superior apical dominance with a single dominant leader. Common seedling Live Oak trees observed by the inventor have a spreading growth habit where the width of the canopy substantially exceeds the height of the tree. In 'FBQV22', however, the tree forms a very dense, distinctive and desirable upright, pyramidal growth habit. There are also an unusual number of temporary secondary spur branches held along main branches and trunk. Secondary spur branches are branches that typically grow to about twelve inches to eighteen inches and then stop growing. These secondary spur branches eventually die and are shed.

Branches arise at wide angles (most lateral branches have branch crotch angles greater than sixty degrees), minimizing formation of included bark. Short well spaced scaffold lateral branches make this plant easier to prune into a strong structure with a central leader. The canopy is very dense with interior and exterior foliage provided by temporary interior spur branches. This new variety is easy to root. For example, in a specific observation, there was a greater than fifty percent take rate for cuttings directly from the initially discovered tree and, in another observation, about seventy percent of the cuttings from two to three year old second-generation trees rooted.

As only observed in some generation progeny trees that had a damaged central leader, as a juvenile tree, the 'FBQV22' cultivar appears to show a strong propensity to reestablish the central leader if damage removes the central leader. This habit is not known to occur in seedling trees or other varieties observed by the inventor.

This extremely high asexual reproduction rate was obtained by preparing the cutting wood in the following manner:

a.) Six to eight inch-long stem and terminal cuttings, each with their bottom one and one half inches of leaves are removed leaving each with seven to nine leaves, were collected in the last week of May from progeny trees.

b.) Cuttings were quick dipped in a solution of 10,000 ppm of KEBA (Potassium salt Indole-3-butyric acid) and 5000 ppm of KNAA (Potassium salt naphthalene acetic acid).

c.) Cuttings were placed in two and one quarter inch by four inch air root pruning containers, filled with appropriate media.

d.) Plants were placed in a mist house and misted with two seconds mist spray every five to six minutes.

e.) Plants remained in the mist house for ten to twelve weeks. Seventy percent of these cuttings rooted.

The 'FBQV22' variety has a higher growth rate compared to common seedling Live Oak trees observed by the inventor and growing in the same area. The trunk diameter, taken at twelve inches above ground of the initially discovered tree of the new variety, at the age of five years and growing in Zolfo Springs, Fla., measured approximately four inches caliper, while common seedling Live Oak trees of the same age and observed by the inventor growing in the same area had a three to four inch caliper. The initially discovered tree and asexually propagated progeny have an upright habit and a dominant leader.

BRIEF DESCRIPTION OF THE DRAWINGS

The accompanying photographs depict the color of the tree and foliage of my new variety as nearly as is reasonably possible to make the same in a color illustration of this character.

DETAILED BOTANICAL DESCRIPTION

Figure 1:
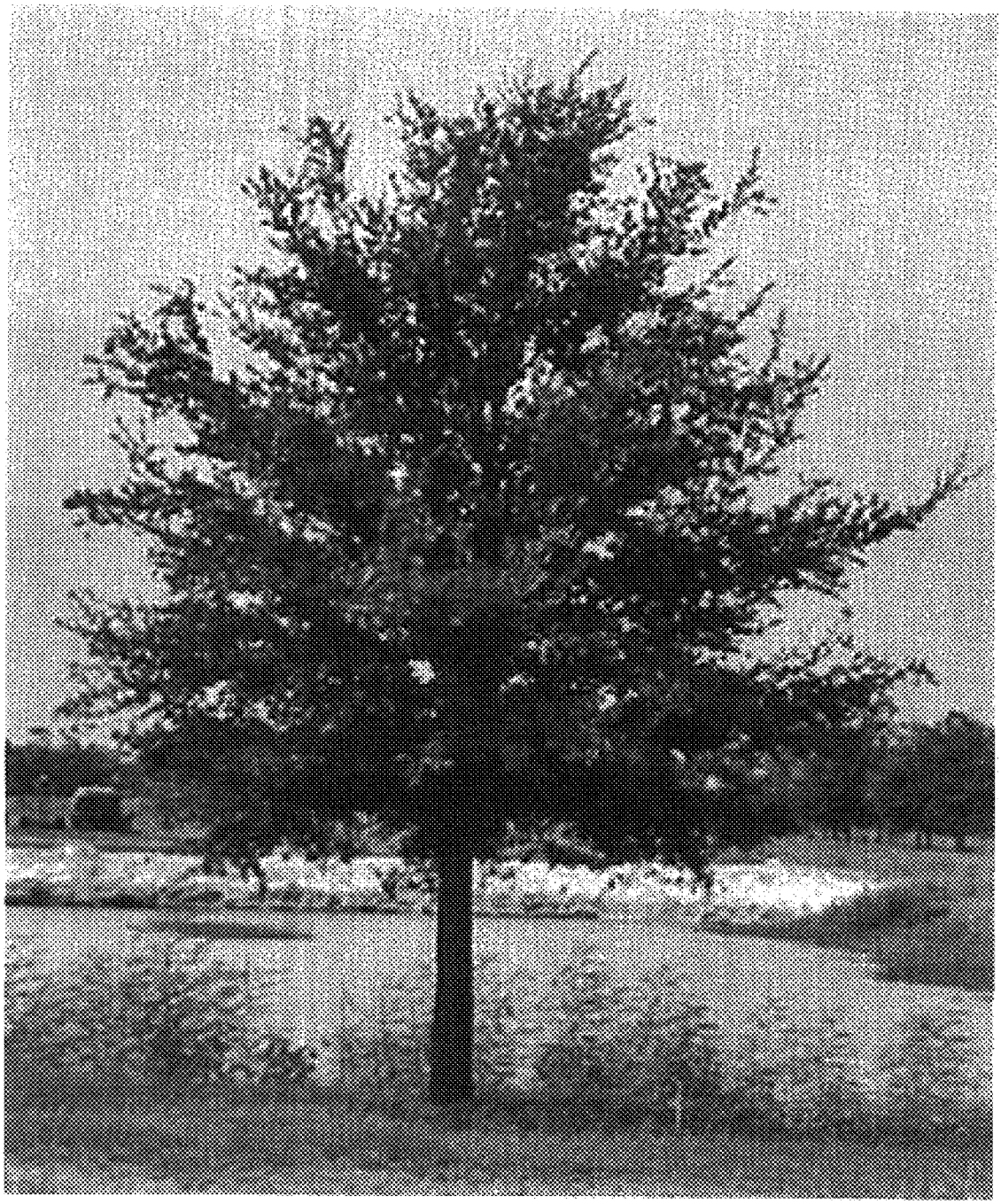
FIG. 1 depicts the initially discovered tree of my new variety showing the pyramidal canopy shape, upright habit, and a single, dominant leader. When this picture was taken, the initially discovered tree was nine years of age, was twenty one feet tall by fifteen feet wide with a nine and one half inch caliper, measured at twelve inches from the ground and was growing in Zolfo Springs, Fla.
Figure 2:
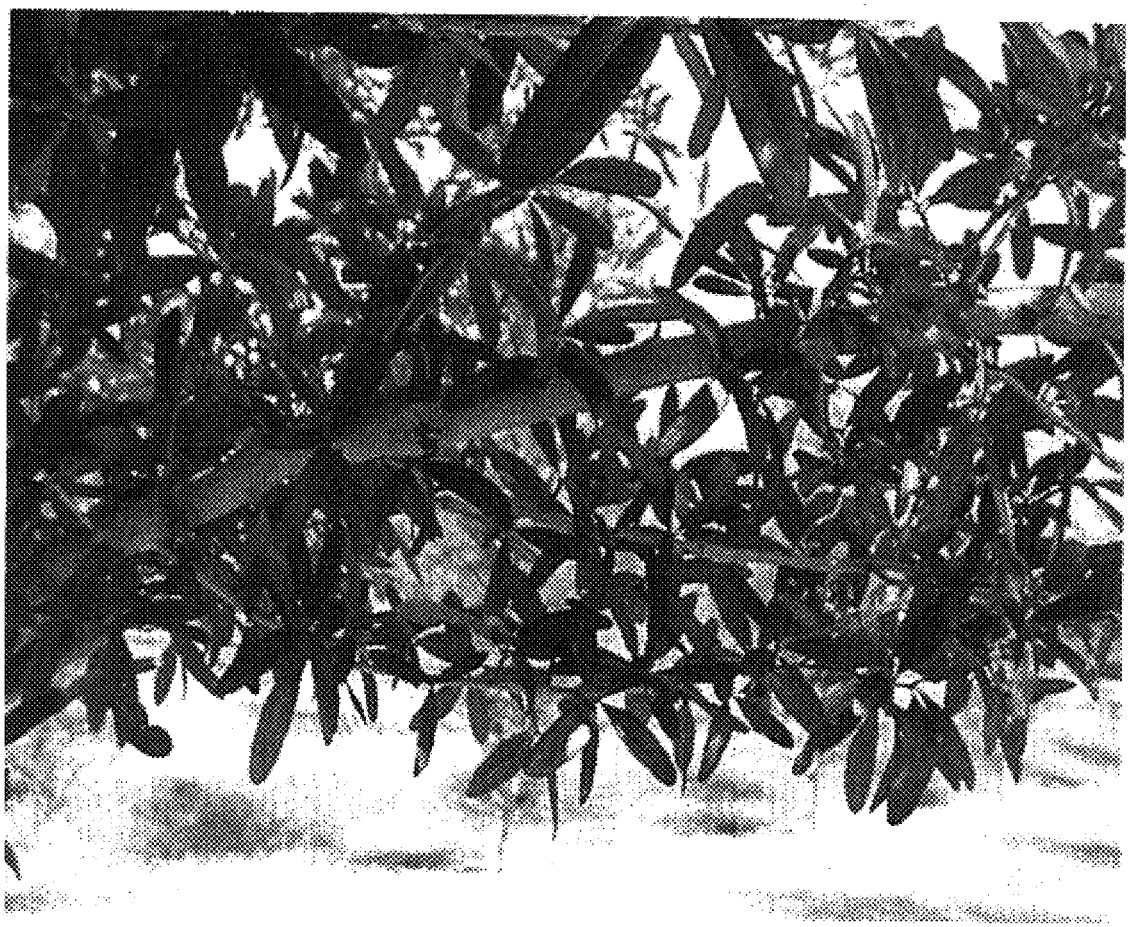
FIG. 2 shows the dense arrangement of spur branches along a main branch.
Figure 3:
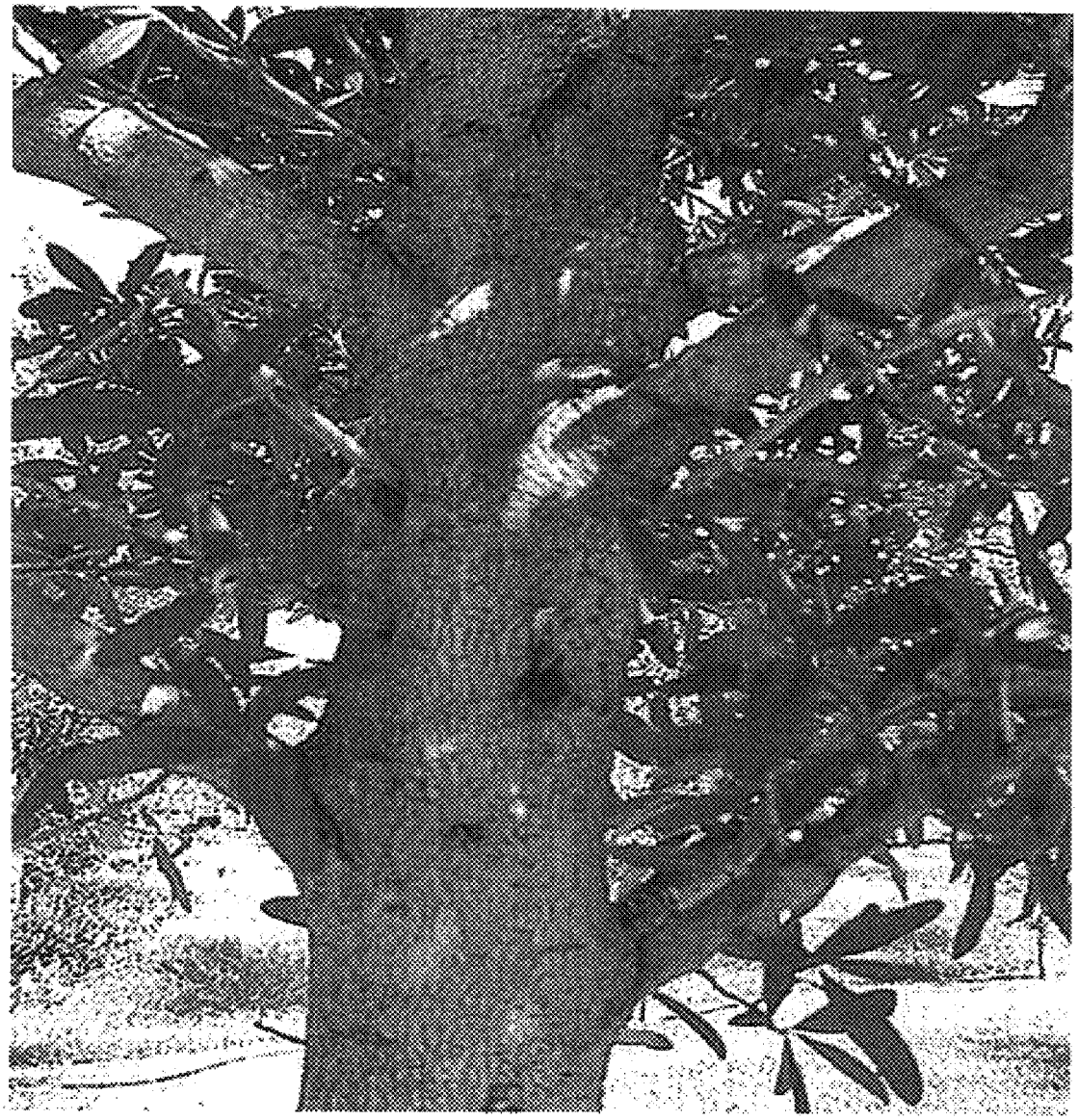
FIG. 3 shows branches arising at a wide angle and lack of included bark.

The following is a description of my new variety of Live Oak tree. Except as otherwise indicated, the observations are of the original tree at age nine years from acorn. Color terminology is in accordance with The Royal Horticultural Society Colour Chart (R.H.S.), except where the context indicates a term having it ordinary dictionary meaning. All color measurements were taken under bright shade conditions.

All Live Oak trees of my new variety, insofar as have been observed, have been identical in all characteristics described below. Other than as set below, as of this time no other characteristics have been observed which are different from common seedling Live Oak trees which have been observed by the inventor.

Parentage: Seedling of unknown parentage.

*Locality where grown and observed.*—Zolfo Springs, Fla. and Sarasota, Fla.

Leaves:

*Shape and arrangement.*—Simple leaves; elliptic to oblong or obovate; alternate arrangement; Base — typically acute, sometimes observed as cuneate to rounded; Apex — typically acute, sometimes observed as obtuse; prominent mid-rib underneath with typically ten to eleven main veins from the mid-rib, vein color typically yellow-green (RHS yellow-green 150B); Margin — entire with occasional acute lobes or teeth; slightly tomentose underneath; stiff; slight downward recurved margin. Size — Length — variable, typically one and one-quarter inches to two and one-half inches, most average one and one-half inches; Width — variable, typically three-eighths to one-half inch, most average three-eighths inch.

*Color.*—Evergreen tree with leaves that shed as the tree buds. Emerging leaves — typical upper surface, maroon to red-purple (RHS red-purple 178B); typical lower surface, yellow-green (RHS yellow-green 148C); Young summer leaves — typical upper surface, dark green (RHS dark green 137A); typical lower surface, dark yellow-green (RHS yellow-green 146B); Mature summer leaves — typical upper surface, dark yellow-green (RHS yellow-green 147A); typical lower surface dark yellow-green (RHS yellow-green 146B).

*Petiole.*—Length — variable, typically one-sixteenth to one-eighth inch long; Width — variable, typically one-thirty-second inch to one-sixteenth inch wide; Color — variable, upper surface color observed as yellow-green (from RHS yellow-green 151C to RHS yellow-green 151D); lower surface color observed as yellow-green (from RHS yellow-green 151C to RHS yellow-green 151D). Slight red coloration on upper surface near to twig (RHS greyed-red 179B).

Buds:

*Shape.*—Variable, subglobose to globose, typically globose.

*Size.*—Length — variable, typically one-thirty-second inch to one-sixteenth inch; Width — variable, typically one-thirty-second inch to one-sixteenth inch.

*Color.*—Greyed-orange (RHS greyed-orange 175B).

Flowers and reproductive organs:

*Location.*—Typical of species — male in catkins, female in axils of leaves.

*Initial flowering season.*—March in Central Florida.

Fruit: Acorns: (observed in both original tree and progeny):

*Number in clusters.*—The initially discovered tree has produced acorns typical of the species; typically one acorn per cluster, sometimes observed as two acorns per cluster.

*Maturation.*—Acorns mature in one growing season and typically fall from the tree in October through November in Central Florida.

*Shape.*—Acorns are oval to ovate and are short and pointed at the apex; no circular scar observed at the base.

*Size.*—Typical observed acorns were three-fourths inch to seven-eighths inch in length and three-eighths inch to seven-sixteenths inch wide.

*Color.*—Typical upper acorn coloration, under the acorn cap, colored greyed-orange (RHS greyed-orange 165C) and typical lower acorn coloration is brown (RHS brown 200C).

Acorn caps:

*Size.*—Typical acorn cap is three-eighths inch to seven-sixteenths inch in width, and three-eighths inch in length; typical peduncle is one-fourth inch to three-eighths inch long and one-sixteenth inch to three-thirty-seconds inch in diameter.

*Color.*—Acorn cap typically colored green (RHS green 138D), and scaly with a finely serrated edge; typical peduncle is colored greyed-brown (RHS greyed-brown 199B). No spots have been observed on the cap.

Stem:

*Color.*—Emerging young stems maroon (RHS red-purple 178B) turning light gray (RHS grayed-green 197C). Mature stems greyed-green (RHS greyed-green 197D).

*Description.*—Glabrous.

Branch attachment: Branches of a five year old tree are typically five to six feet in length and three quarter inch to one inch in diameter, measured at a distance of six inches from the main trunk; branches arise randomly at a typical branch angle of sixty to seventy degrees from the main trunk, (typically greater than sixty degrees), other than spur branches, branches on this tree were spaced four to ten inches apart.

Trunk:

*Color.*—Light grey (RHS greyed-green 197B) becoming slightly fissured and darker (RHS 198C) on older sections. Smooth texture.

Growth habit: Upright, pyramidal.

Vigor: The initially discovered tree and young rooted plants have been observed to grow about three feet in height each year, and the trunk diameter has been observed to increase in caliper about one and one quarter inch each year after the first year.

Propagation: Holds to distinguishing characteristics through succeeding propagation by rooted cuttings.

Disease and pest resistance: Gall insects sometimes found on small branches and leaves; no other diseases or insects observed on trees to date.

I claim:

1. A new and distinct variety of Live Oak (*Quercus virginiana*) tree named 'FBQV22', substantially as herein shown and described.

* * * * *